(12) United States Patent
Wachi et al.

(10) Patent No.: US 6,774,931 B1
(45) Date of Patent: Aug. 10, 2004

(54) INSPECTION METHOD AND DEVICE BY MOVEMENT OF THE FIELD OF VIEW OF THE CAMERA

(75) Inventors: Akihiko Wachi, Nakakoma-gun (JP); Masaya Matsumoto, Kofu (JP); Nobuyasu Nagafuku, Kofu (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 0 days.

(21) Appl. No.: 09/550,998

(22) Filed: Apr. 18, 2000

(30) Foreign Application Priority Data

Apr. 27, 1999 (JP) .......................................... 11-119757

(51) Int. Cl.[7] ................................................ H04N 7/18
(52) U.S. Cl. ............................ 348/87; 348/95; 716/15
(58) Field of Search ......................... 348/87, 95, 125, 348/126, 133; 716/15; H04N 7/18

(56) References Cited

U.S. PATENT DOCUMENTS

| 4,978,224 A | | 12/1990 | Kishimoto et al. |
| 6,023,569 A | * | 2/2000 | Yun .............................. 716/15 |

FOREIGN PATENT DOCUMENTS

| EP | 0685732 | 12/1995 |
| EP | 0718623 | 6/1996 |
| EP | 0841558 | 5/1998 |

* cited by examiner

*Primary Examiner*—Young Lee
(74) *Attorney, Agent, or Firm*—Jordan and Hamburg LLP

(57) ABSTRACT

An algorithm for determining the movement of camera for automatic tracing of inspection positions is preset based on the characteristic shape of the component. A start point and an end point of inspection of lands are designated to the camera, and the camera moves from the start point to the end point automatically along a predetermined path in accordance with the preset algorithm, thereby performing inspection of lands in succession.

20 Claims, 9 Drawing Sheets

INSPECTION METHOD AND DEVICE BY MOVEMENT OF THE FIELD OF VIEW OF THE CAMERA

BACKGROUND OF THE INVENTION

1. Technical Field of the Invention

The present invention relates to an inspection method and device for inspecting electrodes of electronic components, lands on a printed circuit board substrate, or the condition of cream solder printed on the lands by means of a screen printing apparatus or the like.

2. Description of Related Art

For production of electronic circuit boards, various types of electronic components 2–4 are mounted on a printed circuit board substrate as shown in FIG. 3. Such components include, for example, a ball grid array (BGA) type chip 2 in which a multiplicity of electrodes are arranged in a matrix fashion, a quad flat package (QFP) type chip 3 in which a multiplicity of electrodes are projected on four sides thereof, and small out-line package (SOP) type chip 4 with electrodes on both sides thereof. For bonding these components 2–4, lands 5–7 are preliminarily formed on the substrate, and cream solder is printed in register with these lands 5–7 with the use of a screen printing apparatus as shown in FIGS. 4A and 4B.

A screen 8 has apertures 9–11 at positions corresponding to each of the lands 5–7. A camera 12 is provided for taking images of the cream solder printed on the lands 5–7 on the substrate 1. The images are then processed for the purpose of inspection. The camera 12 is constructed to be movable in X and Y directions. Each of the positions of the lands 5–7 to be inspected is designated in advance to the camera, so that the camera moves automatically from one land to the other in succession for inspecting the lands. The camera 12 is connected to a video monitor, with which the image taken by the camera 12 is shown on the display.

Camera teaching of inspection positions is carried out as described below with reference to FIG. 8 and FIG. 9. At step 1 (#1), a group of lands for mounting an electronic component to be inspected is selected. At step 2 (#2), an operator moves the camera while monitoring the position of the camera on the video monitor 13 to a position where the lands 5–7 to be inspected can be seen in the video monitor 13. The number of lands which will fit in the screen of the video monitor, or, the number of lands within the field of view of the inspection screen provided by the camera 12 is limited as shown in FIG. 9 because of the resolution of the camera 12. Accordingly, after designating the initial inspection position, if it is judged at step 3 (#3) that there is a next inspection position to be designated, the procedure returns to step 2, and the next inspection position is designated by moving the camera 12 in a similar manner as described above. The foregoing operation is repeated until inspection positions for all of the lands have been designated.

For example, in the case of BGA type chip 2, each of the nine inspection positions arranged in a matrix fashion as shown in FIG. 9A are designated to the camera by positioning the camera at each of the inspection positions one after another. In the case of QFP type chip 3, each of the twelve inspection positions surrounding the perimeter of the component in a rectangular fashion as shown in FIG. 9B are designated to the camera one after another. Such camera teaching of the inspection positions is necessary for all of the lands 5–7 corresponding to all of electrodes on the electronic components 2–4 to be mounted on the substrate. Moreover, such camera teaching is done for inspection of both lands 5–7 on the substrate 1 and apertures 9–11 in the screen 8.

However, there are quite a large number of lands for bonding electrodes of electronic components especially of the types mentioned above such as BGA, QFP, and SOP. Therefore, teaching of the inspection positions, or the position of the camera which determines the field of view 14 of the inspection screen, takes time as it entails positioning of the camera at each of the inspection positions, with attendant loss in production.

SUMMARY OF THE INVENTION

In view of the foregoing, an object of the present invention is to provide an inspection method and device, with which teaching operation of inspection positions for the camera to perform land inspection is simplified with enhancement in operation efficiency.

To accomplish the above object, the present invention provides an inspection method for inspecting electrodes of electronic components or lands formed on a circuit board substrate corresponding to the electrodes of the electronic components to be mounted on the circuit board substrate, comprising the steps of: teaching an inspection starting point to a camera by positioning the camera at the inspection starting point where a predetermined number of electrodes or lands come within a field of view of the camera; and moving the field of view of the camera automatically in succession along a predetermined path corresponding to the shape of the electronic component from the inspection starting point to an inspection end point by a preset algorithm.

While novel features of the invention are set forth in the preceding, the invention, both as to organization and content, can be further understood and appreciated, along with other objects and features thereof, from the following detailed description and examples when taken in conjunction with the attached drawings.

DETAILED DESCRIPTION OF PREFERRED EMBODIMENTS

Preferred embodiments of the present invention will be hereinafter described with reference to the accompanying drawings.

In the following embodiments, examples are shown wherein the inspection device of the present invention is incorporated in a screen printing apparatus for printing cream solder on lands on a printed circuit board substrate, but the present invention device can of course be provided independently of the screen printing apparatus for the purpose of inspecting the status of cream solder printed on lands.

Figure 3:
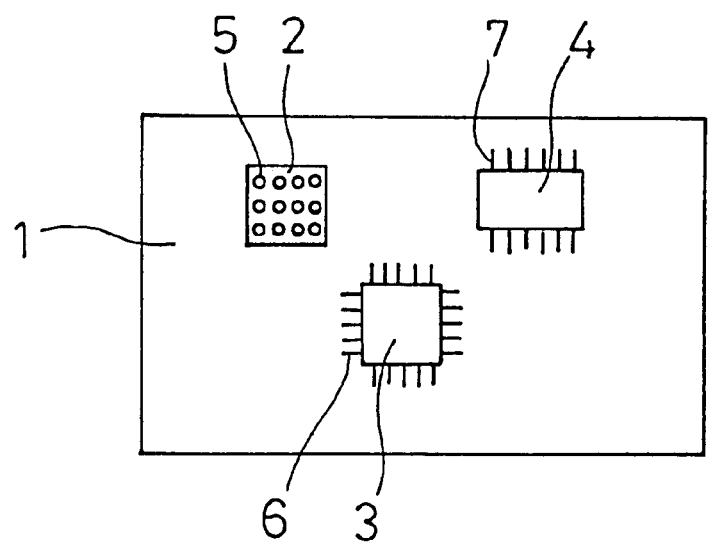
FIG. 3 is a top plan view showing one example of arrangement of various components on a printed circuit board substrate.
Figure 4A:
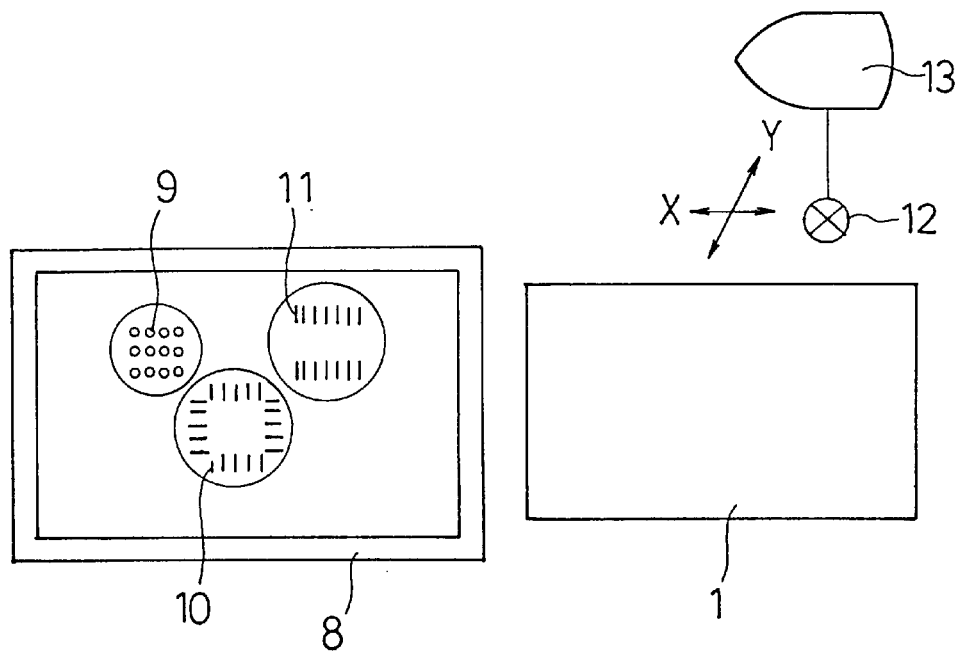
FIG. 4A is a top plan view and FIG. 4B is a vertical sectional front view showing a schematic construction of a screen printing apparatus.
Figure 4B:
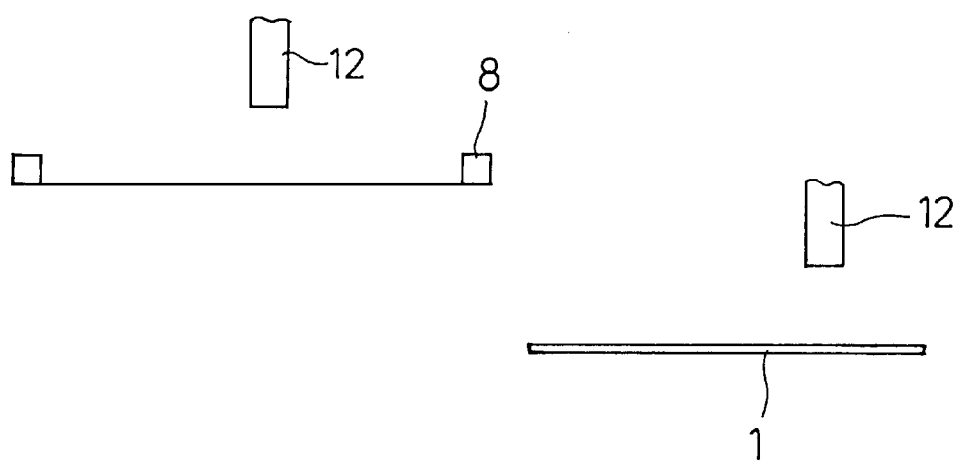

One embodiment of the inspection method according to the present invention is described below by referring to FIG. 1 and FIG. 2. The construction of the printed circuit board substrate and the screen printing apparatus is substantially the same as that shown in FIG. 3 and FIG. 4 and described with respect to the prior art, and common elements are given the same reference numerals.

Figure 1A:
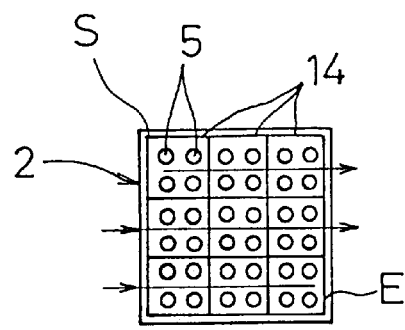
FIGS. 1A–1D are diagrams given in explanation of a method of teaching inspection positions of lands for a BGA type chip according to one embodiment of the present invention.
Figure 1B:
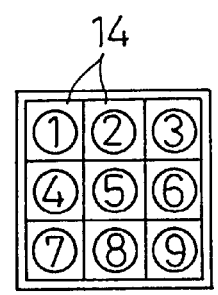
Figure 1C:
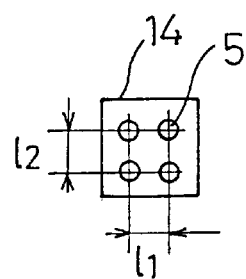
Figure 2A:
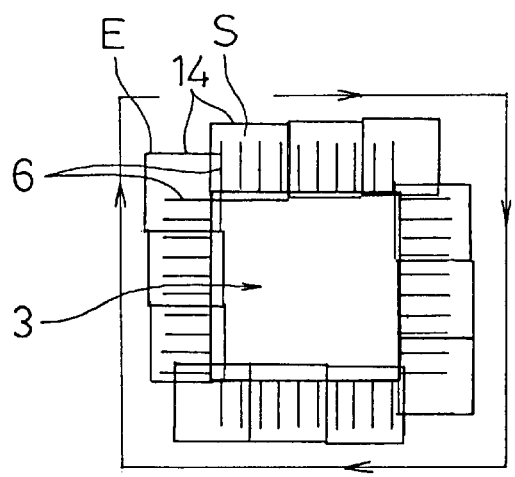
FIGS. 2A–2D are diagrams given in explanation of a method of teaching inspection positions of lands for a QFP type chip.
Figure 2B:
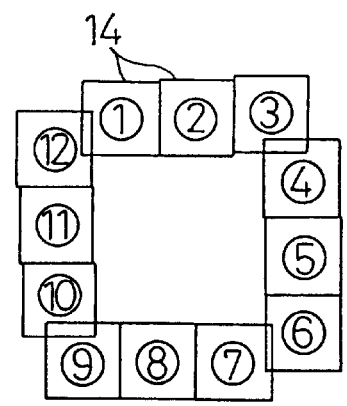

At first, an algorithm is set for moving the field of view of the inspection screen successively from a start point to an end point along a predetermined path corresponding to the characteristic shape of electronic component for which electrodes or lands are to be inspected. Next, the start point and end point of inspection for automatic tracing of inspection screen positions are designated to the camera by positioning the inspection screen at two positions corresponding to the start point and end point. In the case of the BGA type chip 2, two inspection screen positions are set at both ends of the diagonal of the substantially square-shape group of lands corresponding to the shape of the chip denoted at S and E as shown in FIG. 1A. In the case of the QFP type chip 3, two inspection screen positions are set at two adjacent positions at one corner as shown in FIG. 2A. Although not shown, in the case of the SOP type chip 4, two inspection screen positions are set at both ends of the diagonal of the chip.

The land inspection method in the case of the BGA type chip 2 is described in detail with reference to FIGS. 1A–1D. When the teaching of inspection screen positions is effected by positioning the inspection screen at the start point S, the pitch spaces $l_1$, $l_2$ between left and right lands, and between upper and lower lands with respect to the lands 5, 5 at both ends within the field of view 14 of the inspection screen are calculated from the resolution of the camera. Based on the pitch spaces $l_1$, $l_2$ thus obtained, the amount of movement of the camera 12 to the next inspection screen position in the leftward/rightward direction and upward/downward direction is determined. It should be noted that FIGS. 1A–1D are top plan views and upward/downward direction in this description means a direction orthogonal to the leftward/rightward direction in FIG. 1A.

Figure 1D:
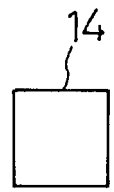

The camera 12 first moves to the start point as taught, where inspection of lands 5 within the field of view 14 is carried out. The camera 12 then moves to the right hand side in FIG. 1A and FIG. 1B by the amount determined from the pitch $l_1$ between left and right lands at the start point to the next inspection screen position. The camera 12 repeats the above actions likewise until it comes to a position where there is no land within the field of view 14 as shown in FIG. 1D. When the camera comes to a position where no lands are detected, it moves downwards in FIG. 1A by the amount determined from the pitch $l_2$ between upper and lower lands at the start point, and further moves to the position right below the start point in FIG. 1A, where land inspection is started again. The camera then moves rightwards as inspection within one field of view is completed, and repeats the actions likewise in the order shown by the arrow in FIG. 1A and denoted at encircled numerals in FIG. 1B. When the camera 12 reaches the end point and completes the inspection of lands within the field of view 14, the inspection of all lands 5 is ended.

When the camera 12 comes to a position where no lands come into the field of view, for example, after inspecting the position denoted at encircled numeral 3, the camera 12 may be moved downwards in the drawing by the predetermined pitch and then leftwards to the position encircled numeral 6, instead of moving the camera 12 back to the position immediately below the inspection start point denoted at S. That way, the movement amount of the camera 12 can be reduced to minimum and thereby the tact time can be decreased.

Figure 2C:
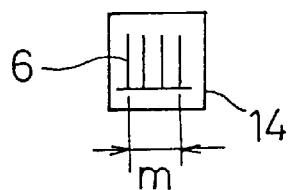

Next, the land inspection method in the case of the QFP type chip 3 is described in detail with reference to FIGS. 2A–2D. When the teaching of inspection screen positions is effected by positioning the inspection screen at the start point S, the pitch space m between the lands 6, 6 at both ends within the field of view 14 of the inspection screen as shown in FIG. 2C are calculated from the resolution of the camera. Based on the pitch m thus obtained, the amount of movement of the camera 12 to the next inspection screen position is determined.

Figure 2D:

The camera 12 first moves to the start point as taught, where inspection of lands 6 within the field of view 14 is carried out. The camera 12 then moves to the right hand side in FIG. 2A by the amount determined from the pitch m between the lands at both ends at the start point to the next inspection screen position. The camera 12 repeats the above actions likewise until it comes to a position where there is no land within the field of view 14 as shown in FIG. 2D. When the camera comes to a position where no lands are detected, the movement of automatic tracing is changed from leftward/rightward direction to upward/downward direction, and the camera moves downwards in succession in FIG. 2A by the amount determined from the pitch m, with land inspection being performed in each field of view of respective inspection screen positions. Next time when the camera comes to a position where there is no land within the field of view 14, the automatic tracing changes its direction from downwards to leftwards. Likewise, the third time when the camera comes to a position where no lands are detected, the movement of automatic tracing is changed from leftwards to upwards. Thus the camera moves in the order as shown by the arrow in FIG. 2A and denoted at encircled numerals in FIG. 2B for continuous inspection of lands. When the camera 12 reaches the end point and completes the inspection of lands 6 within the field of view 14, the inspection of all lands 6 is ended.

In the case of the SOP type chip 4, of which description in detail is omitted as it is similar to the above, two positions at both ends of the diagonal of the chip are designated as the start point and the end point, and the amount of movement of the camera to the next inspection screen position is determined from the pitch space m between the lands at both ends within the field of view at the start point. The camera 12 first moves rightwards in succession, and when it comes to a position where there is no land within the field of view 14, it moves to right below the start point along the line which passes the end point, and starts inspection by continuously moving rightwards toward the end point.

According to the present invention, inspection of lands is performed by automatic tracing of successive inspection positions in accordance with the characteristic shape of each chip to be inspected by only teaching the start point and the end point of the inspection to the camera. As compared to the conventional method which entails teaching of each of the inspection positions by positioning the camera at each of the inspection positions, the present invention method enables highly efficient inspection of lands.

Figure 5:
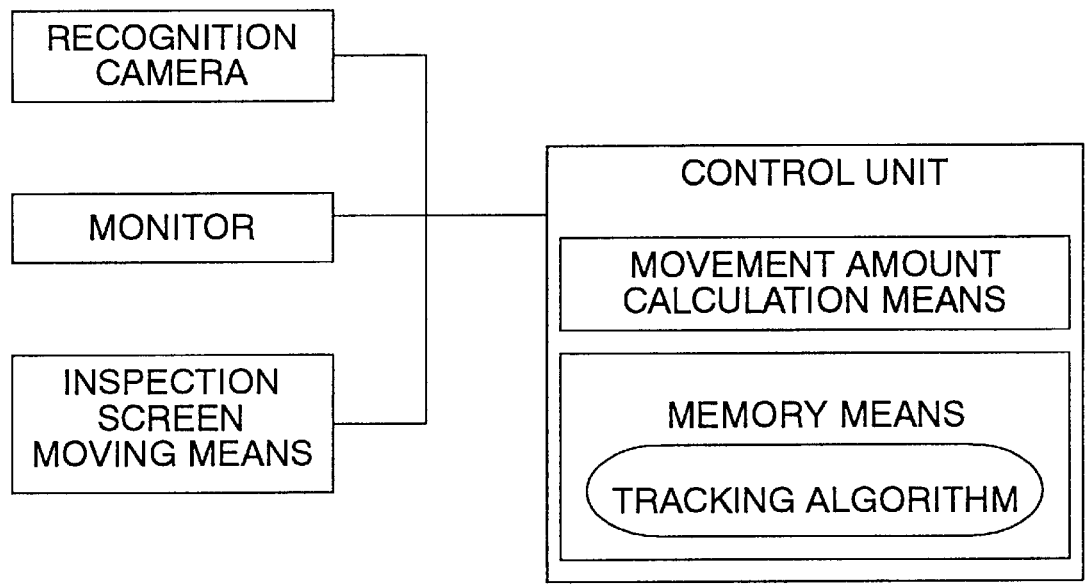
FIG. 5 is a diagram showing the construction of the control unit in the inspection device.

The present invention inspection device is basically constructed as shown in the schematic diagram of FIG. 5. The control unit includes a movement amount calculation means for calculating the pitch space between two lands based on images taken by the camera, and a memory means for storing a tracking algorithm for automatically moving the field of view of the camera in succession along a predetermined path.

The above described inspection method can be applied to the inspection of apertures 9–11 formed in the screen 8 of the screen printing apparatus.

Figure 6:
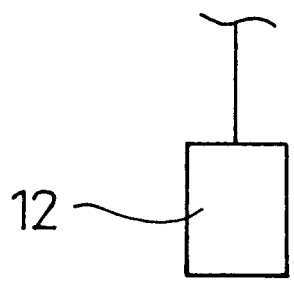
FIG. 6 is a schematic diagram showing one example in which the inspection device is incorporated in a component mounting apparatus.
Figure 6:
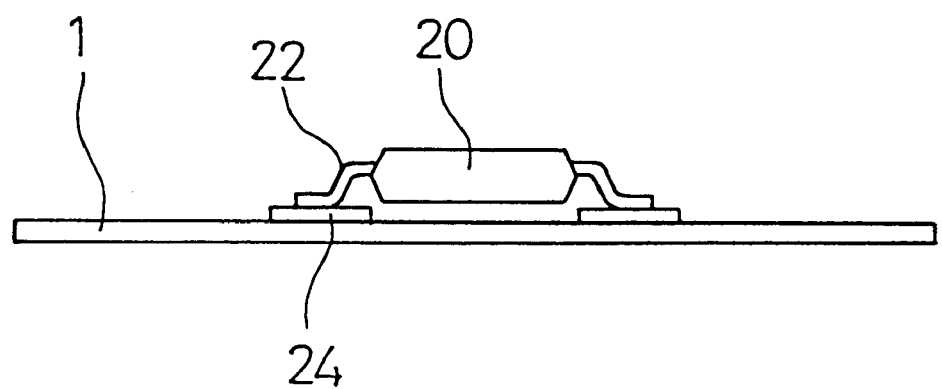
Figure 7:
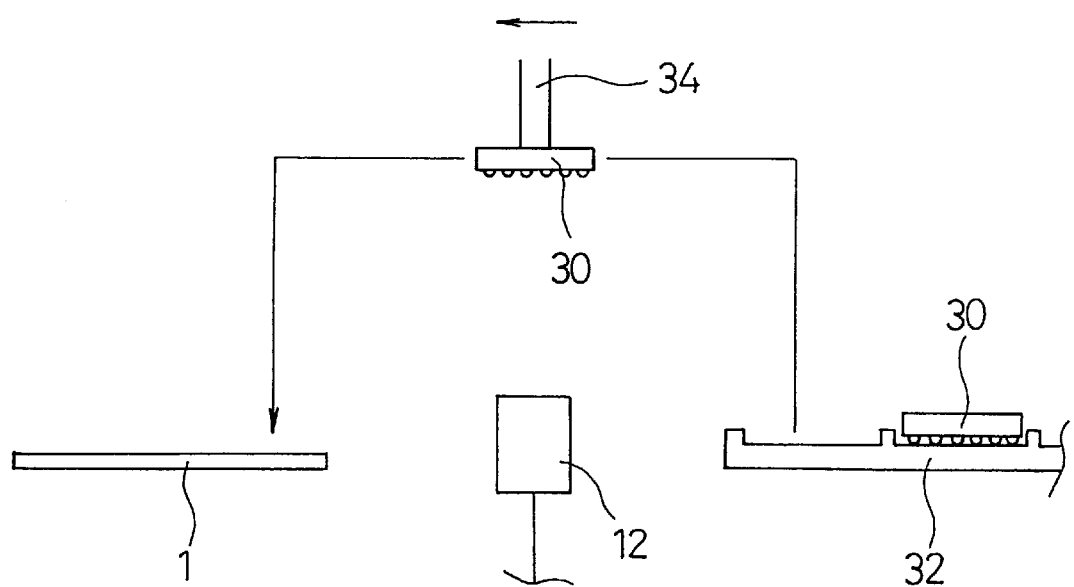
FIG. 7 is a schematic diagram showing another example in which the inspection device is incorporated in a component mounting apparatus.
Figure 8:
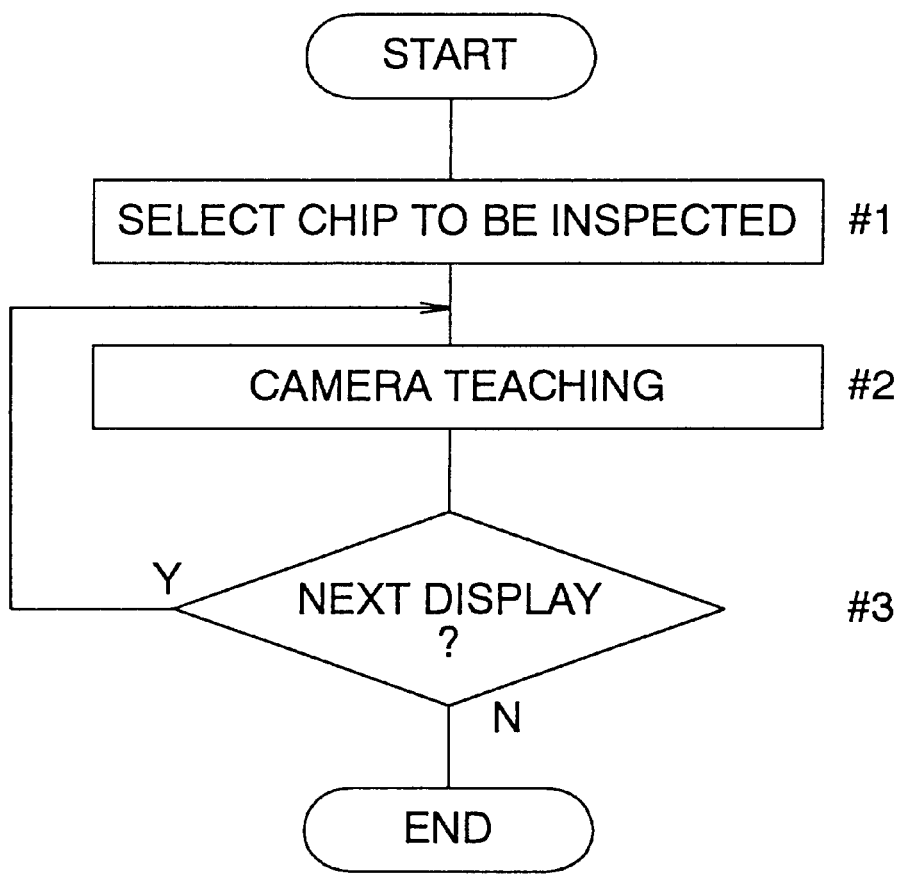
FIG. 8 is a flowchart showing a conventional method of teaching inspection positions of lands.
Figure 9A:
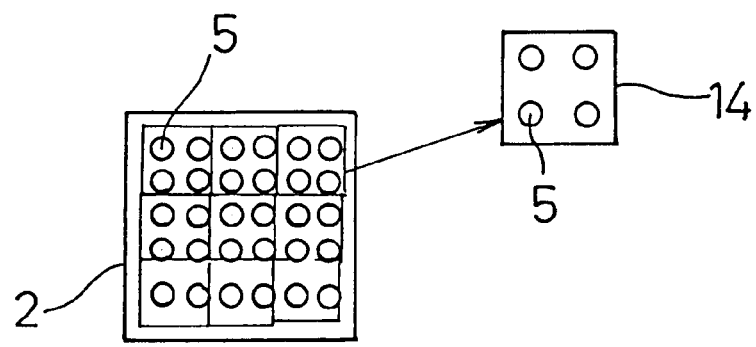
FIGS. 9A and 9B are diagrams given in explanation of a conventional method of teaching inspection positions of lands, FIG. 9A showing the case of a BGA type chip, and FIG. 9B showing the case of QFP type chip.
Figure 9B:
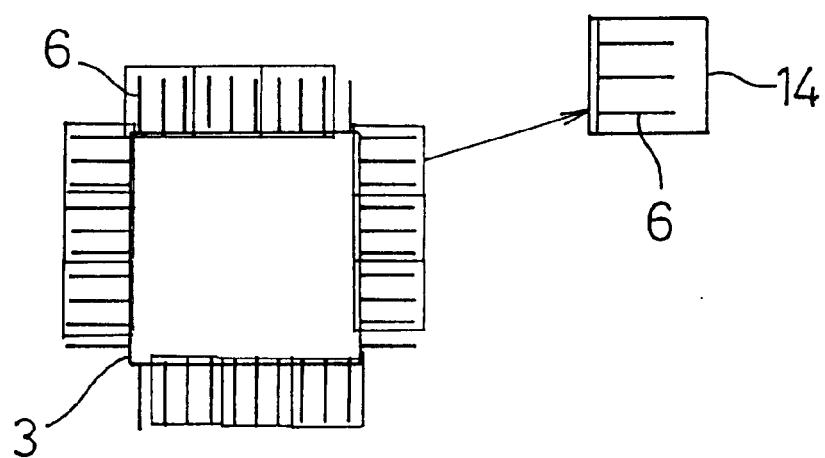

Furthermore, the inspection method and device of the present invention having the construction as described above can also be applied for various inspection purposes in a component mounting apparatus, as shown in FIG. 6 and FIG. 7.

Specifically, as shown in FIG. 6, the present invention inspection method can favorably be applied to the inspection of the lands 24 and electrodes 22 after a component 20 has been mounted onto a circuit board 1. Similarly, the status of the lands and the electrodes after they have been reflow-soldered can also be inspected using the present invention inspection device.

Furthermore, as shown in FIG. 7, the present invention inspection method can also favorably be used for inspecting the status of a component 30 or its electrodes during it is transported by a suction nozzle 34 from a parts feeding section 32 onto the circuit board 1. That is, the present invention can also be applied in the component mounting apparatus for the position correction purpose, i.e., by inspecting the component or its electrodes in accordance with the present invention inspection method, it is possible to detect the amount of displacement of the component held on the suction nozzle, and to correct the position of the component so that it is mounted precisely at a predetermined position on the circuit board 1.

Next, a second embodiment of the inspection method of the present invention will be described.

In this embodiment, the total number of fields of view, i.e., the total number of positions at which the inspection screen of the camera needs to be located for inspecting all of the lands, is preliminarily obtained for each discrete type of component and stored in the memory means of the control unit. That is, for each type of component of which lands are to be inspected, the camera is moved to the designated start position, where the amount of movement is calculated from the pitch space between two lands within the field of view. The camera is moved successively from a position of one field of view to a next position of another field of view by the thus obtained amount along a predetermined path as described in the foregoing, and the total number of fields of view for inspecting all the lands for a specific type of component is obtained.

Thus in the actual operation of inspection, the number of times that the camera is moved from one position to another is 3counted, this being compared to the stored data, and upon a predetermined number of times being reached, it is determined that all of the lands have been inspected, and the inspection operation is ended. With this method, it is not necessary to designate the inspection end point at the initial stage of teaching the inspection start point to the camera, whereby the tact time for one cycle of inspecting an object is reduced, and operation efficiency is increased.

Next, a third embodiment of the inspection method of the present invention will be described.

In this embodiment, similarly to the previously described embodiments, the inspection screen of the camera is located and registered at the start position, where the pitch space between two lands is calculated from the image data for determining the amount of movement of the camera for automatic tracing of the lands. The camera moves from one position, where the lands within the field of view are inspected, to a next position by the obtained amount. In this embodiment, instead of designating the inspection end point to the camera at the initial step, it is determined that the operation should end on condition that there is no land within the field of view when the camera moves to rightward and then returns to a position below the start point. That is, when the camera has reached the position denoted at encircled numeral 9 in FIG. 1B, there will be no land within the field of view when the next time the camera moves rightwards and also when the camera move to a position below the position denoted at encircled numeral 7 in FIG. 1B. Upon such conditions being met, it is judged that all of the lands have been inspected and the operation is ended. Not to mention, this method can advantageously be applied in the case of inspecting lands for BGA type chips or any other objects arrayed in a matrix fashion.

In the case of inspecting lands for QFP chips, it is also possible to detect the end of operation, by the fact that the camera has made a round and inspected all four sides of collective lands and then comes to a position where no land is detected within the field of view.

In either case, it is not necessary to designate the inspection end point at the initial stage of teaching the inspection start point to the camera, whereby the tact time for one cycle of inspecting an object is reduced, and operation efficiency is increased.

Next, a fourth embodiment of the inspection method of the present invention will be described.

Similarly to the previously described embodiments, the inspection screen of the camera is located and registered at the start position, where the pitch space between two lands is calculated from the image data for determining the amount of movement of the camera for automatic tracing of the lands. The feature of this embodiment is that the pitch space obtained at the inspection start point is stored in the memory means of the control unit. This method is particularly advantageous in a case where a number of lands or electrodes of the same shape are to be inspected continuously. Judgement of the end point of inspection may be made in accordance with any of the first to third embodiment methods. Basically, for inspecting a number of lands or electrodes of the same type of component in succession, the pitch space between the lands need not be calculated at the start point each time the inspection is started. Thus it is preferable that the fourth embodiment be used in combination with any of the foregoing embodiments for inspecting a group of lands of the same shape in a continuous manner.

Although the present invention has been fully described in connection with the preferred embodiment thereof, it is to be noted that various changes and modifications apparent to those skilled in the art are to be understood as included within the scope of the present invention as defined by the appended claims unless they depart therefrom.

What is claimed is:

1. An inspection method for inspecting electrodes of electronic components or lands formed on a circuit board substrate corresponding to the electrodes of the electronic components to be mounted on the circuit board substrate, comprising:

setting an algorithm for moving a field of view of a camera in succession from an inspection start point to an inspection end point along a predetermined path corresponding to a shape of the electronic component;

teaching the inspection starting point to the camera by positioning the camera at the inspection starting point where a predetermined number of electrodes or lands come within the field of view of the camera;

obtaining a pitch space between two electrodes or lands within the field of view of the camera when the camera is positioned at the inspection starting point;

determining an amount of movement of the camera from one position to a subsequent position for inspection along the predetermined path based on the pitch space; and moving the field of view of the camera automatically in succession along the predetermined path corresponding to the shape of the electronic component according to the preset algorithm and by the determined amount of movement of the camera from one position to the subsequent position such that the movement of the field of view of the camera is based on the pitch space between two electrodes or lands and inspecting all of the electrodes or lands from the inspection starting point to the inspection end point during movement of the field of view of the camera.

2. The inspection method according to claim 1, further comprising teaching the inspection end point to the camera by positioning the camera at the inspection end point prior to moving the field of view of the camera along the predetermined path.

3. The inspection method according to claim 2, wherein the group of lands are formed in a matrix fashion thereby forming a substantially square shape corresponding to an electronic component having a plurality of electrodes on entire surface thereof in a matrix fashion; and when teaching the inspection starting point and inspection end point to the camera, designating two points at both ends of a diagonal of the square shape of the group of lands as the inspection staring point and the inspection end point, whereby the camera automatically moves in succession by the amount corresponding to the obtained pitch space toward one direction from one inspection position to a subsequent inspection position for inspecting one row of lands, and when completing inspection of the first row of lands, the camera moves on to a next row of lands for inspection thereof until it reaches the inspection end point.

4. The inspection method according to claim 2, wherein the group of lanes are formed in a fashion surrounding a square area corresponding to an electronic component having a plurality of projecting electrodes on four sides thereof; and when teaching the inspection starting point and inspection end point to the camera, designating two adjacent points at one corner of the group of lands as the inspection starting point and the inspection end point, whereby the camera automatically moves in succession by the amount corresponding to the obtained pitch space toward one direction from one inspection position to a subsequent inspection position for inspecting one row of the lands, and when completing inspection of the row of lands, the camera changes its direction of movement at right angles and moves along for inspection of a next row of lands until it reaches the inspection end point.

5. The inspection method according to claim 2, wherein the group of lands are formed in two spaced rows corresponding to an electronic component having a plurality of electrodes on both sides thereof; and when teaching the inspection starting point and inspection end point to the camera, designating two points at both ends of a diagonal connecting one end of one row of the lands to the other end of the other row of the lands as the inspection starting point and the inspection end point, whereby the camera automatically moves from the inspection starting point toward one direction for inspecting one row of the lands, and at an end of the row of lands, the camera moves on to the next row of lands for inspection thereof until it reaches the inspection end point.

6. The inspection method according to claim 1, further comprising:

inputting a total number of fields of view necessary to cover all of the electrodes or lands to be inspected, said total number of fields of view being preliminary obtained and stored; and counting the number of times the camera moves to one position to another along the predetermined path and comparing said number with the stored total number of fields of view, wherein upon said total number of fields of view being reached, the inspection operation is ended.

7. The inspection method according to claim 1, further comprising:

moving the camera in succession by the amount corresponding to the obtained pitch space toward one direction from one inspection position to a subsequent inspection position for inspecting one row of lands, the camera moving on to a next row of lands for inspection thereof, and stopping the inspection operation when no land is detected within the field of view successively at more than two inspection positions.

8. The inspection method according to claim 1, wherein the step of obtaining the pitch space between two electrodes or lands comprises obtaining a first pitch space between laterally adjacent lands within the field of view of the camera and obtaining a second pitch space between vertically adjacent lands within the field of view of the camera.

9. The inspection method according to claim 8, wherein the step of determining the amount of movement of the camera from one position to a subsequent position comprises determining a first amount of movement of the camera when moving laterally from one position to a subsequent position and determining a second amount of movement of the camera when moving vertically from one position to a subsequent position.

10. The inspection method according to claim 1, wherein the pitch space is obtained based on resolution of the camera.

11. The inspection method according to claim 1, wherein only the inspection starting point and the inspection end point are taught to the camera.

12. The inspection method according to claim 1, wherein the amount of movement of the camera from one position to a subsequent position is the same during movement of the camera along the predetermined path from the inspection starting point to the inspection end point.

13. An inspection method for inspecting electrodes of electronic components or lands formed on a circuit board substrate corresponding to the electrodes of the electronic components to be mounted on the circuit board substrate, comprising:

setting an algorithm for moving a field of view of a camera in succession from an inspection start point to an inspection end point along a predetermined path corresponding to a shape of the electronic component;

teaching the inspection starting point to the camera by positioning the camera at the inspection staring point where a predetermined number of electrodes or lands come within the field of view of the camera;

obtaining a pitch space between two electrodes or lands of the same electronic component of each respective electronic component within the field of view of the camera;

determining an amount of movement of the camera based on the obtained pitch space;

inputting the determined amount of movement of the camera from one inspecting position to a subsequent inspecting position along a predetermined path; and moving the field of view of the camera automatically in succession along the predetermined path corresponding to the shape of the electronic component from the inspection starting point to the inspection end point according to the preset algorithm.

14. The inspection method according to claim 13, wherein the step of obtaining the pitch space between two electrodes or lands comprises obtaining a first pitch space between laterally adjacent lands within the field of view of the camera and obtaining a second pitch space between vertically adjacent lands within the field of view of the camera.

15. The inspection method according to claim 14, wherein the step of determining the amount of movement of the camera comprises determining a first amount of movement of the camera when moving laterally from one position to a subsequent position and determining a second amount of movement of the camera when moving vertically from one position to a subsequent position.

16. The inspection method according to claim 13, wherein the pitch space is obtained based on resolution of the camera.

17. The inspection method according to claim 13, wherein only the inspection stating point and the inspection end point are taught to the camera.

18. The inspection method according to claim 13, wherein the pitch space is obtained when the camera is positioned at the inspection starting point.

19. An inspection device for inspecting electrodes of electronic components or lands formed on a circuit board substrate corresponding to the electrodes of the electronic components to be mounted on the circuit board substrate, comprising:

a camera for taking images of the electrodes or lands, said camera having a movable field of view;

an inspection screen moving means for moving the field of view of the camera in succession from one point to a subsequent point of a respective electronic component, an inspection starting point being taught to the camera by positioning the camera at the inspection starting point where a predetermined number of electrodes or lands come within the field of view of the camera; and a control unit including a movement amount calculation means for determining an amount of movement of the field of view of the camera, means for setting an algorithm for moving the field of view of the camera in succession from the inspection start point to an inspection end point along a predetermined path corresponding to a shape of each respective electronic component, and a memory means for storing the algorithm, said movement amount calculation means being arranged to obtain a pitch space between two electrodes or lands within the field of view of the camera when the camera is positioned at the inspection starting point such that the amount of movement of the field of view of the camera from one point to the subsequent point is based on the pitch space, the inspection screen moving means being arranged to move the field of view of the camera automatically in succession alone the predetermined path corresponding to the shape of each respective electronic component according to the set algorithm and by the determined amount of movement of the field of view of the camera from one point to the subsequent point such that all of the electrodes or lands from the inspection starting point to the inspection end point are inspected during movement of the field of view of the camera.

20. A screen printing apparatus comprising:

a screen having apertures formed therein;

means for printing cream solder on lands formed on a circuit board substrate through said screen; and an inspection device for inspecting the lands on the circuit board including a camera for taking images of the lands, said camera having a movable field of view, an inspection screen moving means for moving the field of view of the camera in succession from one point to a subsequent point of a respective electronic component, an inspection starting point being taught to the camera by positioning the camera at the inspection starting point where a predetermined number of lands come within the field of view of the camera, and a control unit including a movement amount calculation means for determining an amount of movement of the field of view of the camera, means for setting an algorithm for moving the field of view of the camera in succession from the inspection start point to an inspection end point along a predetermined path corresponding to a shape of the electronic component, and a memory means for storing the algorithm, said movement amount calculation means being arranged to obtain a pitch space between two electrodes or lands within the field of view of the camera when the camera is positioned at the inspection starting point such that the amount of movement of the field of view of the camera from one point to the subsequent point is based on the pitch space, the inspection screen moving means being arranged to move the field of view of the camera automatically in succession along the predetermined path corresponding to the shape of the electronic component according to the set algorithm and by the determined amount of movement of the field of view of the camera from one point to the subsequent point such that all of the lands from the inspection starting point to the inspection end point are inspected during movement of the field of view of the camera.

* * * * *